United States Patent
Knoer

(10) Patent No.: US 10,662,293 B2
(45) Date of Patent: *May 26, 2020

(54) METHOD FOR PRODUCING SPHERICAL POLYSILSESQUIOXANE PARTICLES

(71) Applicant: Wacker Chemie AG, Munich (DE)

(72) Inventor: Sebastian Knoer, Emmerting (DE)

(73) Assignee: WACKER CHEMIE AG, Munich (DE)

( * ) Notice: Subject to any disclaimer, the term of this patent is extended or adjusted under 35 U.S.C. 154(b) by 45 days.

This patent is subject to a terminal disclaimer.

(21) Appl. No.: 16/068,007

(22) PCT Filed: Oct. 6, 2016

(86) PCT No.: PCT/EP2016/073902
§ 371 (c)(1),
(2) Date: Jul. 3, 2018

(87) PCT Pub. No.: WO2018/065058
PCT Pub. Date: Apr. 12, 2018

(65) Prior Publication Data
US 2019/0002642 A1    Jan. 3, 2019

(51) Int. Cl.
*C08G 77/06*   (2006.01)
*C08G 77/18*   (2006.01)
*A61K 8/891*   (2006.01)
*C08G 77/04*   (2006.01)
*A61Q 19/00*   (2006.01)
*A61K 8/02*    (2006.01)
*C08G 77/32*   (2006.01)
*C08G 77/00*   (2006.01)

(52) U.S. Cl.
CPC ............. *C08G 77/06* (2013.01); *A61K 8/025* (2013.01); *A61K 8/891* (2013.01); *A61Q 19/00* (2013.01); *C08G 77/045* (2013.01); *C08G 77/32* (2013.01); *A61K 2800/10* (2013.01); *C08G 77/70* (2013.01)

(58) Field of Classification Search
None
See application file for complete search history.

(56) References Cited

U.S. PATENT DOCUMENTS

| | | | | |
|---|---|---|---|---|
| 4,113,665 A | * | 9/1978 | Law | C08G 77/06 524/779 |
| 4,373,060 A | * | 2/1983 | Ching | C08G 77/26 106/287.12 |
| 4,935,484 A | * | 6/1990 | Wolfgruber | C08G 77/06 528/34 |
| 6,376,078 B1 | * | 4/2002 | Inokuchi | C08J 3/12 427/212 |
| 7,897,714 B2 | | 3/2011 | Lee et al. | |
| 2004/0143081 A1 | * | 7/2004 | Oikawa | C07F 7/21 528/10 |
| 2007/0092821 A1 | * | 4/2007 | Sato | G03G 9/0806 430/108.4 |
| 2007/0249854 A1 | * | 10/2007 | Kim | A61K 8/02 556/419 |
| 2008/0004359 A1 | * | 1/2008 | Ma | C08J 3/09 516/104 |
| 2008/0008944 A1 | * | 1/2008 | Sato | G03G 9/0819 430/48 |
| 2008/0226998 A1 | * | 9/2008 | Ishii | G03G 9/0804 430/48 |
| 2010/0222503 A1 | * | 9/2010 | Laine | C08G 77/045 524/588 |
| 2014/0069488 A1 | * | 3/2014 | Tanaka | G06F 3/045 136/252 |
| 2015/0013763 A1 | * | 1/2015 | Matsumura | H01B 1/22 136/256 |
| 2015/0013764 A1 | * | 1/2015 | Matsumura | H01B 1/22 136/256 |
| 2017/0253781 A1 | * | 9/2017 | Kashio | C08K 3/00 |
| 2017/0267904 A1 | * | 9/2017 | Nakayama | C08K 3/00 |
| 2019/0202992 A1 | * | 7/2019 | Knoer | A61K 8/025 |

FOREIGN PATENT DOCUMENTS

| | | | |
|---|---|---|---|
| CN | 104744700 A | | 7/2015 |
| JP | 4088023 A2 | | 3/1992 |
| JP | 6060239 B2 | | 8/1994 |
| JP | 6248081 A2 | | 9/1994 |
| JP | 10045914 A2 | | 2/1998 |
| JP | 2000186148 A2 | | 7/2000 |
| JP | 2001354770 A | * | 12/2001 |
| JP | 2003183396 A | | 7/2003 |
| JP | 2003335860 A2 | | 11/2003 |
| JP | 3740449 B2 | | 2/2006 |
| JP | 2008127564 A | | 6/2008 |

OTHER PUBLICATIONS

Database WPI Week 200055 Thomson Scientific, London, GB; AN 2000-581615 XP002763905.
Database WPI Week 200422 Thomson Scientific, London, GB; AN 2004-230738 XP002763904.
Database WPI Week 199817 Thomson Scientific, London, GB; AN 1998-189384 XP002763903.
Related U.S. Appl. No. 16/066,129, filed Jun. 26, 2018.

* cited by examiner

*Primary Examiner* — Peter A Salamon
(74) *Attorney, Agent, or Firm* — Brooks Kushman P.C.

(57) ABSTRACT

Spherical silsesquioxane particles are formed by controlled hydrolysis of trialkoxysilane(s) in acidic media, followed by addition of base, storage for at least 2 hours, and spray drying. Essentially non-agglomerated spherical particles are produced without milling.

19 Claims, No Drawings

METHOD FOR PRODUCING SPHERICAL POLYSILSESQUIOXANE PARTICLES

CROSS REFERENCE TO RELATED APPLICATIONS

This application is the U.S. National Phase of PCT Appln. No. PCT/EP2016/073902 filed Oct. 6, 2016, the disclosure of which is incorporated in its entirety by reference herein.

BACKGROUND OF THE INVENTION

1. Field of the Invention

The invention relates to a process for producing spherical polysilsesquioxane particles by hydrolysis of trialkoxysilane, condensation of the hydrolyzate and spray drying of the particles, and to the polysilsesquioxane particles.

2. Description of the Related Art

The prior art, for example JP3970449B2, JPH06248081A and JPH0488023A, discloses various processes for producing spherical polymethylsilsesquioxane particles. JP3970449B2 describes optimization of the space-time yield and control of the particle size. Drying results in a melting of the particles and the construction of a network structure. To afford pulverulent products the molten particles are inconveniently obtained by subsequent milling.

The required processing step of milling, which is costly and laborious, is a disadvantage. After drying, the highly voluminous and dusty polysilsesquioxane particles must initially be packed. This entails material losses and cleaning costs for the packing plant. The material must subsequently be transported to the mill. Due to the low bulk density of the polysilsesquioxane particles very large containers are required which renders transport and intermediate storage inconvenient and costly. At the mill the material must be transferred again. This entails further material losses and in addition protective measures must be taken for protecting coworkers from the non-toxic but very dusty material. There are further material losses in the mill through abrasion or broken particles on account of the comparatively harsh conditions.

No process has hitherto been described which allows control of the agglomerization behavior of the particles.

SUMMARY OF THE INVENTION

The present invention provides a process for producing spherical polysilsesquioxane particles in which in a first step trialkoxysilane of general formula (I)

$$RSi(OR^1)_3 \qquad (I),$$

in which
R represents a hydrocarbon radical having 1 to 16 carbon atoms whose carbon chain may be interrupted by nonadjacent —O— groups, and
$R^1$ represents a $C_1$- to $C_4$-alkyl radical,
is reacted with acidified water having a pH of not more than 6 with commixing to afford a hydrolyzate,
in a second step the hydrolyzate is mixed with a solution of a base in water or $C_1$- to $C_4$-alkanol,
in a third step the mixture is stored for at least 2 h, and in a fourth step the polysilsesquioxane particles are spray-dried.

DETAILED DESCRIPTION OF THE PREFERRED EMBODIMENTS

It was found that agglomerization-free spherical polysilsesquioxane particles are obtainable when the particles are isolated directly from the dispersion by spray drying. This affords disagglomerated particles in only one processing step. Transport-, processing- and cleaning-intensive open powder handling, which is necessary for a separate drying and subsequent milling, can thus be avoided. The polysilsesquioxane particles are dispersed under very gentle conditions. Material losses by abrasion or broken particles, as can occur in the mill, are markedly reduced in spray drying.

Such particles exhibit highly advantageous behavior, in particular for cosmetic applications. They are converted into a liquid-like flowable state (fluidization) even at low shear and are therefore exceptionally easy to spread and provide a velvety skin feel. This behavior is not observable for agglomerated particles; these undergo balling upon spreading on the skin.

Fluid, i.e. liquid-like, behavior is apparent in particular immediately after shaking of the polysilsesquioxane particles. The greater the volume increase, the more pronounced the fluid behavior. A material which exhibits a 50% volume increase already shows fluid behavior which for example manifests itself in that the material in the container—immediately after shaking—flows to and fro similarly to a liquid upon tilting of the container. A material with a 50% volume increase undergoes very rapid sedimentation and returns into the non-fluid initial state which is disadvantageous. The spherical polysilsesquioxane particles preferably show at least a 100% volume increase.

The polysilsesquioxane particles preferably comprise at least 30% by weight, more preferably at least 40% by weight, and most preferably at least 50% by weight, of a sieve fraction<20 µm.

The polysilsesquioxane particles preferably comprise at least 60% by weight, more preferably at least 70% by weight, of a sieve fraction<40 µm.

The polysilsesquioxane particles preferably comprise less than 25% by weight, more preferably less than 20% by weight, and most preferably less than 15% by weight, of a sieve fraction>100 µm.

R preferably represents an alkyl radical having 1 to 6 carbon atoms or phenyl radical, in particular the ethyl radical or the methyl radical.

$R^1$ preferably represents a methyl, ethyl or n-propyl radical, in particular a methyl radical.

Preferred trialkoxysilanes of general formula (I) are methyltrimethoxysilane, methyltriethoxysilane, methyltri-n-propoxysilane, methyltriisopropoxysilane and methyltris(2-methoxyethoxy)silane and mixtures thereof.

The reaction to afford a hydrolyzate is preferably effected in acidified water having a pH of not more than 5.5, more preferably not more than 4.5 and preferably at least 1, more preferably at least 2, and in particular at least 2.3.

The water employed is preferably deionized, and before acidification preferably has a conductivity of not more than 50 µS/cm, more preferably not more than 30 µS/cm, yet more preferably not more than 20 µS/cm, and especially not more than 10 µS/cm auf, in each case measured at 20° C.

The water employed may be acidified using Brønsted acids or Lewis acids.

Examples of Lewis acids are $BF_3$, $AlCl_3$, $TiCl_3$, $SnCl_4$, $SO_3$, $PCl_5$, $POCl_3$, $FeCl_3$ and hydrates thereof, and $ZnCl_2$. Examples of Brønsted acids are hydrochloric acid, hydrobromic acid, sulfuric acid, nitric acid, nitrous acid, chlorosulfonic acid, phosphoric acids such as ortho-, meta- and polyphosphoric acids, boric acid, selenous acid, nitric acid, carboxylic acids such as formic acid, acetic acid, propionic acid, citric acid and oxalic acid, haloacetic acids such as trichloroacetic and trifluoroacetic acid, p-toluene sulfonic acid, acidic ion exchangers, acidic zeolites, and acid-activated Fuller's earth.

Hydrochloric acid, hydrobromic acid and acetic acid are preferred.

The acidification of the water may be effected before the conversion to the hydrolyzate, simultaneously with the conversion or both before the conversion and simultaneously with the conversion. In one particular embodiment the water is partly acidified with hydrochloric acid before the reaction to afford the hydrolyzate and a further portion of hydrochloric acid is introduced via the trialkoxysilanes of general formula (I).

The hydrolysis of the trialkoxysilane is a weakly exothermic reaction. In a preferred embodiment the temperature in the first step is preferably maintained, optionally by heating or cooling, at 0° C. to 60° C., more preferably at 10° C. to 50° C., particularly preferably at 15° C. to 40° C., still more preferably at 15° C. to 30° C., and in particular at 15-25° C., wherein the temperature variation after attainment of the target temperature is by preference less than 10° C., more preferably less than 5° C. The metered addition of the trialkoxysilane may be commenced before or after attainment of the target temperature, as desired.

In another embodiment the trialkoxysilane is added rapidly, e.g. in one portion. The heat is not actively or only partly removed by cooling. In this embodiment an exothermic increase in temperature takes place after addition of the trialkoxysilane. The temperature of the reaction in the first step is 20° C. to 80° C., preferably up to 60° C.

It is preferable for the trialkoxysilane to be metered in over 0.5 to 5 h, more preferably not more than 2 h. Between rapid addition and metered addition there is a fluid transition of inventive embodiments, i.e. it is possible for example to effect addition rapidly in 15 min with partial removal of heat up to not more than 40° C. or it is possible to effect metered addition for example over 2 h but only perform a low level of cooling, thus initially allowing a temperature increase to 30° C. and maintaining at this temperature.

Metered addition at a constant temperature is particularly preferred.

It is preferable when in the first step 5 to 43 parts by weight, more preferably 11 to 34 parts by weight, and in particular 13 to 25 parts by weight of trialkoxysilane are added per 100 parts by weight of water.

Commixing in the first step may be effected by means of a static mixer, or preferably by means of a stirrer.

It is preferable when, after metered addition of the trialkoxysilane, the mixture is subjected to further stirring for 5 min to 5 h, more preferably 10 min to 3 h, and in particular 15 min to 1.5 h. The further stirring time is preferably chosen such that the sum of the addition time for the silane and the further stirring time do not exceed 6 h. The temperature during the further stirring is maintained at 0° C. to 60° C., preferably at 10° C. to 50° C., more preferably at 10° C. to 40° C., yet more preferably at 10° C. to 30° C., and in particular at 15° C. to 25° C. It is preferable when the difference in the temperature of the reaction in the first step and the temperature during the further stirring is less than 20° C., more preferably less than 10° C., and in particular less than 5° C.

It is preferable when, in the second step, the base is selected from alkali metal hydroxide, alkaline earth metal hydroxide, alkali metal methoxide, ammonia and organic amines. Preferred organic amines are alkyl amines such as mono-, di- or triethylamine, mono-, di- or trimethylamine or 1,2-ethylenediamine. It is preferable to employ the hydroxides of Li, Na, K. It is preferable to employ a solution of alkali metal hydroxide in water or in an alkanol having 1 to 3 carbon atoms. Preferred alkanols are 1-propanol, 2-propanol, ethanol and in particular methanol. A solution of ammonia or alkali metal hydroxide in water is likewise preferred. Diluted or concentrated solutions of alkali metal hydroxide of 0.001 to 1100 g/l at 20° C., preferably 0.01 to 500 g/l, more preferably 0.1 to 500 g/l, are suitable.

When using a solution of alkali metal hydroxide in an alkanol having 1 to 3 carbon atoms the particles exhibit reduced adhesion to one another, show a reduced degree of agglomeration and have a lower propensity for clumping. The particles show a drier skin feel preferred in cosmetic applications.

KOH is preferred as the alkali metal hydroxide.

Also possible as an alternative to NaOH and KOH is the use of an NaOH- or KOH-former which in the second step immediately reacts with the water present in the hydrolyzate to afford NaOH or KOH. Examples thereof are sodium methoxide, potassium methoxide, NaH and KH. In this embodiment the use of sodium methoxide or potassium methoxide in methanolic solution is preferred.

It is preferable when sufficient solution of base is added to ensure that a pH of at least 6, more preferably at least 6.5, and not more than 10, more preferably not more than 9.5 is achieved in each case immediately after addition of the base. The particle size may be influenced by the addition of the amount of base, wherein low pH values result in larger particles. The especially preferred pH is 7.5 to 9.

The solution of base is preferably added over 10 seconds to 10 minutes, in particular over 1 to 3 minutes, preferably with vigorous and short stirring.

In a preferred embodiment the temperature of the addition of base in the second step is maintained by preference at 0° C. to 60° C., more preferably at 10° C. to 50° C., yet more preferably 10° C. to 40° C., still more preferably at 10° C. to 30° C., and in particular at 15° C. to 25° C. It is preferable when the difference in the temperature during further stirring and the temperature during addition of base is less than 20° C., more preferably less than 10° C., and in particular less than 5° C.

Commixing in the second step may be effected by means of a static mixer or preferably by means of a stirrer.

After the second step the commixing is preferably terminated within 10 minutes, more preferably within 5 minutes. After the second step the mixture is by preference not moved for at least 1 h, more preferably at least 1.5 h, and most preferably at least 2.5 h. A stirrer may subsequently be switched on at a low speed to prevent sedimentation of the particles. This is optional and not necessary since the sedimented polysilsesquioxane particles may be stirred up readily.

After the second step the temperature of the mixture is by preference altered by not more than 20° C., preferably not more than 10° C., for at least 1 h, more preferably at least 1.5 h, and most preferably at least 2.5 h.

If in the starting phase in the third step, in which the formation of the particles is effected, the mixture is moved, this results in an increased incident of malformed, coalesced or agglomerated particles.

In a preferred embodiment in the third step the mixture is not moved until isolation of the polysilsesquioxane particles.

It is preferable when in the third step, the mixture is stored for at least 4 h, more preferably at least 7 h, and in particular at least 10 h, before the polysilsesquioxane particles are isolated. Storage times of up to 12 weeks are also possible.

A clouding is usually visible even after 1-30 minutes.

The temperature in the third step is by preference 0° C. to 60° C., preferably at 10° C. to 50° C., yet more preferably 10° C. to 40° C., still more preferably 10° C. to 30° C., and in particular 15° C. to 25° C. Low temperatures form larger particles and higher temperatures form smaller particles.

At a temperature of 15° C. to 25° C. there is little if any temperature gradient in the reaction mixture toward the outer region, thus a minimal thermal gradient between the reactor wall and the reaction solution and thus minimized thermal convection during the precipitation of the particles.

The process according to the invention may be run as a batch, semi-batch or continuous process.

In a preferred embodiment the mixture is neutralized by addition of an acid after the third step.

In a preferred embodiment the particles are isolated, preferably by filtration or centrifugation, after the third step. After isolation the particles are preferably washed with a washing liquid which is preferably selected from DM water, methanol, ethanol and mixtures thereof. The washed particles are redispersed with a liquid which is preferably selected from DM water, methanol, ethanol and mixtures thereof. The obtained dispersion preferably comprises 5% to 50% by weight, particularly preferably 10% to 35% by weight, in particular 10% to 25% by weight, of particles.

If volatile bases, such as many organic amines, are used, for example di- or triethylamine or ammonia, washing is preferably omitted.

The use of ammonia as the base is advantageous since here both the base itself and the resulting salt of the base are volatile under the conditions of spray drying.

From the mixture obtained in step 2 or from the dispersion obtained by isolating, washing and redispersing, a dry, free-flowing powder is produced in the spray dryer. Depending on the alcohol content of the mixture the drying gas employed is air or inert gas, for example nitrogen, argon, helium, or lean air comprising not more than 2% oxygen.

The spray drying may be performed in any of the well-known apparatuses suitable for spray drying of liquids, for example those having at least one two-material nozzle, a hard metal or hollow cone nozzle or a swirl atomization nozzle, or having a rotating atomization disk in a heated dry gas stream. It is preferable when the entry temperature of the dry gas stream, which is preferably air, lean air or nitrogen, into the spray-drying apparatus is 110° C. to 350° C., more preferably at least 150° C. and not more than 300° C., and in particular at least 200° C. and not more than 280° C. The exit temperature of the gas stream formed during drying is preferably 40° C. to 200° C., in particular 100° C. to 180° C. The spray pressure is preferably at least 500 hPa, more preferably at least 800 hPa, preferably not more than 500,000 hPa, and in particular not more than 10,000 hPa. The rotational speed of the atomization nozzle is especially between 4000 and 50,000 rpm.

In a particular embodiment the spray-dried polysilsesquioxane particles are afterdried, for example in a paddle dryer, fluidized bed dryer, tray dryer, flow dryer or drum dryer.

Particles which are dried for a long time at an exit temperature of 110° C. are dry but have a high Si—OH content. At 140° C. the Si—OH content is markedly reduced but not yet fully removed; at 160° C. Si—OH groups are again significantly reduced. A reduced Si—OH content affords advantages in the spreading behavior and in the fluidization of the particles.

The polysilsesquioxane particles preferably exhibit a spherical shape upon examination in an electron microscope. The spherical polysilsesquioxane particles preferably exhibit an average sphericity y of at least 0.6, in particular at least 0.7. The spherical polysilsesquioxane particles preferably have an average roundness x of at least 0.6, in particular at least 0.7. The roundness x and sphericity y may be determined according to DIN EN ISO 13503-2, page 37, annex B.3, in particular figure B.1.

It is preferable when all process steps are performed at the pressure of the ambient atmosphere, i.e. about 0.1 MPa (abs.);

they may also be performed at higher or lower pressures. Preference is given to pressures of at least 0.08 MPa (abs.) and more preferably at least 0.09 MPa (abs.), and preferably not more than 0.2 MPa (abs.), in particular not more than 0.15 MPa (abs.).

All of the abovementioned symbols of the abovementioned formulae are each defined each independently of one another. The silicon atom is tetravalent in all formulae.

In the examples which follow unless otherwise stated all amounts and percentages are based on weight, all pressures are 0.10 MPa (abs.) and all temperatures are 20° C.

EXAMPLES

Volume-Weighted Particle Size Distribution $D_{50}$

Determination of the volume-weighted particle size distribution is by means of static laser diffraction with the Sympatec HELOS instrument fitted with a RODOS dry disperser with 2 bar of compressed air as the dispersion medium, according to ISO 13320. The $d_{50}$ indicates the median particle size.

Sieve Analysis:

Sieve analysis was by means of dry sieving using a Retsch AS 200 basic analytical sieve machine at 100% amplitude. For analysis four sieves according to DIN ISO 3310 having the following mesh sizes were stacked: 200 μm, 100 μm, 40 μm, 20 μm, bottom. In each case 50 g of substance were applied atop the first sieve (200 μm) and sieved for 10 minutes.

Determination of Fluidization and Volume Increase:

6.0 g of polysilsesquioxane particles are introduced into a 50 ml PP centrifuge tube, shaken vigorously for 30 seconds and left to stand for 1 h on a level plane. If required a level surface is subsequently generated by light tapping. The (settled) volume of the sample is read off. The container is sealed and shaken vigorously for at least 30 seconds until all of the material is dispersed. The centrifuge tube is placed straight back on the plane and the (shaken) volume read off immediately thereafter. Shaking and reading off is repeated a total of three times and from the determined values the average volume (shaken, average of three experiments) determined. The volume increase is then calculated with the following formula:

Volume increase=volume(shaken,average of three experiments)×100/volume(settled)

The microscopic examinations were performed with a Zeiss SUPRA 55 VP scanning electron microscope. Prior to examination the samples were splattered with gold to prevent charging phenomena using a Safematic CCU-010 sputter coater.

The spherical polysilsesquioxane particles of examples 1 to 3 have an average sphericity y of 0.8 and an average roundness x of 0.85 according to DIN EN ISO 13503-2, page 37, annex B.3, figure B.1.

EXAMPLES

Example 1

1328 g of demineralized water having a conductivity of 0.1 µS/cm is initially charged into a glass flask and temperature-controlled to 20° C. The flask contents are stirred at 300 rpm. The pH is adjusted to a value of 4.40 by addition of 0.1 molar hydrochloric acid. 291.6 g of methyltrimethoxysilane are metered in over 1 h and the temperature is maintained at 20° C. After termination of the metered addition the flask contents are stirred at 20° C. for 1 h. 65.49 g of 0.1 molar methanolic KOH solution are added over 1 min at 20° C. and mixed for a total of 3 min to form a homogeneous mixture. The stirrer is then switched off. After 21 h the precipitated particles are filtered off, washed with DM water and redispersed with DM water to afford a 15% suspension. The suspension is then dried with a Niro Mobile Minor laboratory spray dryer at an entry temperature of 260° C. and an exit temperature of 155-160° C. and using nitrogen as the drying gas.

Example 2

The example is performed according to the process of example 1, except that 85.14 g of 0.1 molar methanolic KOH solution are added to achieve precipitation.

Example 3

The example is performed according to the process of example 1, except that 7.96 g of 1 molar aqueous ammonia solution are added to achieve precipitation.

Comparative Example C1

The example is performed according to the process of example 1, except that the precipitated particles are filtered off, washed with DM water and dried in a drying cabinet at 150° C. for 18 h.

Comparative Example C2

The particles from the noninventive comparative example C1 are dispersed in an Alpine 100AFG fluidized bed opposed jet mill at a pressure of 5 bar and a sifter speed of 4000 rpm.

Comparative Example C3

The example is performed according to the process of example 3, except that the precipitated particles are filtered off, washed with DM water and dried in a drying cabinet at 150° C. for 18 h.

Comparative Example C4

The particles from the noninventive comparative example C3 are dispersed in an Alpine 100AFG fluidized bed opposed jet mill at a pressure of 7 bar and a sifter speed of 12,000 rpm.

TABLE 1

| | | Example | | | | | | |
|---|---|---|---|---|---|---|---|---|
| | | 1 | 2 | 3 | C1* | C2* | C3* | C4* |
| Precipitation base | | KOH (MeOH) | KOH (MeOH) | Ammonia | KOH (MeOH) | KOH (MeOH) | Ammonia | Ammonia |
| Precipitation time** | hrs. | 21 | 21 | 21 | 21 | 21 | 21 | 21 |
| Milling | | no | no | no | no | yes | no | yes |
| Spray drying | | yes | yes | yes | no | no | no | no |
| Sieve fraction | <20 µm | 81 | 80 | 35 | 67 | 78 | 1 | 35 |
| Sieve fraction | 20-40 µm | 7 | 6 | 54 | 17 | 15 | 16 | 55 |
| Sieve fraction | 40-100 µm | 9 | 9 | 6 | 9 | 4 | 41 | 5 |
| Sieve fraction | 100-200 µm | 2 | 3 | 3 | 5 | 2 | 27 | 3 |
| Sieve fraction | >200 µm | 1 | 2 | 2 | 3 | 1 | 15 | 2 |
| Sum of fractions <40 µm | | 88 | 86 | 89 | 84 | 93 | 17 | 90 |
| Sum of fractions >100 µm | | 3 | 5 | 5 | 8 | 3 | 68 | 5 |
| Median particle size $d_{50}$ | µm | 6.12 | 4.14 | 4.22 | 5.51 | 5.51 | 4.22 | 4.22 |

*noninventive
**hold time in hours after base addition

The invention claimed is:
1. A process for producing spherical polysilsesquioxane particles, comprising:
  in a first step, reacting trialkoxysilane(s) of formula (I)

$$RSi(OR^1)_3 \qquad (I),$$

in which
  R represents a hydrocarbon radical having 1 to 16 carbon atoms whose carbon chain is optionally interrupted by nonadjacent —O— groups,
  $R^1$ represents a $C_1$- to $C_4$-alkyl radical,
  with acidified water having a pH of not more than 6 to form a hydrolysate;

in a second step, mixing the hydrolyzate with a solution of a base in water or in $C_1$- to $C_4$-alkanol;

in a third step, storing the mixture of the second step for at least 2 h without substantial agitation, forming polysilsesquioxane particles;

and in a fourth step, spray drying the polysilsesquioxane particles in the mixture or recovered therefrom.

2. The process of claim 1, in which R represents an ethyl radical or a methyl radical.

3. The process of claim 1, in which $R^1$ represents an ethyl radical or a methyl radical.

4. The process of claim 1, in which in the first step, 5 to 43 parts by weight of trialkoxysilane are added per 100 parts by weight of water.

5. The process of claim 1, in which in the second step, a solution of ammonia in water or alkali metal hydroxide in an alkanol having 1 to 3 carbon atoms is employed.

6. The process of claim 1, in which sufficient solution of base is added to ensure that a pH of 6.5 to 9.5 is achieved, measured immediately after addition of base.

7. The process of claim 5, in which sufficient solution of base is added to ensure that a pH of 6.5 to 9.5 is achieved, measured immediately after addition of base.

8. The process of claim 1, in which the temperature of the addition of base in the second step is 10° C. to 40° C.

9. The process of claim 1, in which in the third step, the mixture is stored for at least 7 h prior to spray drying.

10. The process of claim 1, in which after the third step the mixture is neutralized by addition of an acid.

11. The process of claim 9, in which after the third step the mixture is neutralized by addition of an acid.

12. The process of claim 1, in which after the third step the particles are isolated and washed with a washing liquid, and the washed particles are redispersed with a liquid, prior to spray drying.

13. The process of claim 1, in which an entry temperature of a dry gas stream into a spray-drying apparatus used for spray drying in the fourth step is 110° C. to 350° C.

14. The process of claim 1, wherein step b) immediately follows step a).

15. The process of claim 1, wherein an exit temperature from a spray dryer employed in step d) is at least 110° C.

16. The process of claim 1, wherein an exit temperature from a spray dryer employed in step d) is at least 140° C.

17. The process of claim 1, wherein an exit temperature from a spray dryer employed in step d) is at least 160° C.

18. The process of claim 1, further comprising after-drying the polysilsesquioxane particles obtained from step d).

19. The process of claim 18, wherein the step of after-drying takes place in at least one of a paddle dryer, fluidized bed dryer, tray drier, flow drier, or drum drier.

* * * * *